(12) United States Patent
Tourrel

(10) Patent No.: US 10,926,082 B2
(45) Date of Patent: Feb. 23, 2021

(54) IMPLANTABLE ELECTRODE ARRAY

(71) Applicant: Oticon Medical A/S, Smørum (DK)

(72) Inventor: Guillaume Tourrel, Vallauris (FR)

(73) Assignee: OTICON MEDICAL A/S, Smørum (DK)

( * ) Notice: Subject to any disclaimer, the term of this patent is extended or adjusted under 35 U.S.C. 154(b) by 163 days.

(21) Appl. No.: 16/190,468

(22) Filed: Nov. 14, 2018

(65) Prior Publication Data

US 2019/0143100 A1   May 16, 2019

(30) Foreign Application Priority Data

Nov. 15, 2017  (EP) .................... 17201787

(51) Int. Cl.
*A61N 1/05*   (2006.01)
*H05K 1/11*   (2006.01)

(52) U.S. Cl.
CPC ........... *A61N 1/0541* (2013.01); *H05K 1/118* (2013.01); *H05K 2201/056* (2013.01)

(58) Field of Classification Search
CPC . A61N 1/0541; H05K 1/118; H05K 2201/056
USPC ....................................................... 607/137
See application file for complete search history.

(56) References Cited

U.S. PATENT DOCUMENTS

| | | | |
|---|---|---|---|
| 4,532,930 A * | 8/1985 | Crosby | A61N 1/36038 607/57 |
| 6,070,105 A | 5/2000 | Kuzma | |
| 6,374,143 B1 | 4/2002 | Berrang et al. | |
| 2004/0030376 A1 | 2/2004 | Gibson et al. | |
| 2004/0172118 A1 | 9/2004 | Gibson | |
| 2011/0016710 A1 | 1/2011 | Dadd et al. | |
| 2011/0071596 A1* | 3/2011 | Kara | B82Y 30/00 607/57 |
| 2011/0098719 A1* | 4/2011 | Llinas | A61B 34/30 606/129 |
| 2012/0004715 A1* | 1/2012 | Ramachandran | A61N 1/0541 607/137 |
| 2013/0211485 A1* | 8/2013 | Govindarajan | A61N 1/0531 607/116 |
| 2016/0193460 A1* | 7/2016 | Xu | B29C 51/02 607/137 |
| 2017/0113046 A1* | 4/2017 | Fried | A61B 5/055 |

\* cited by examiner

*Primary Examiner* — Erin M Piateski
(74) *Attorney, Agent, or Firm* — Birch, Stewart, Kolasch & Birch, LLP

(57) ABSTRACT

An implantable electrode array comprising a flexible electrically non-conductive carrier, a flexible electrically non-conductive substrate provided with a plurality of electrical tracks. At least two of the plurality of electrical tracks run along different lengths of the flexible substrate. Each of the plurality of electrical tracks is physically and electrically connected to a respective electrode contact of a plurality of electrode contacts. The flexible substrate is immovably attached to and along a length of the flexible carrier.

19 Claims, 7 Drawing Sheets

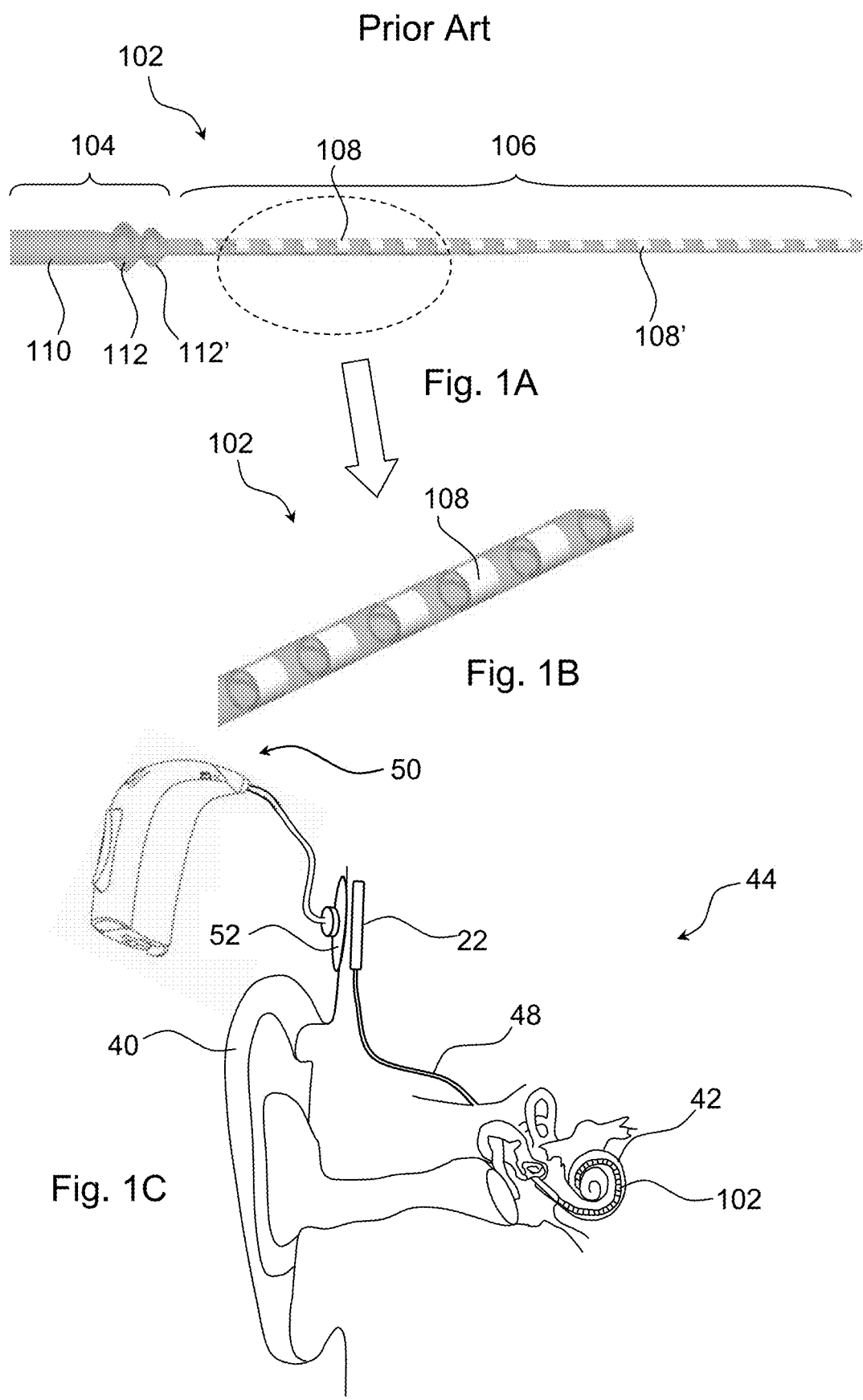

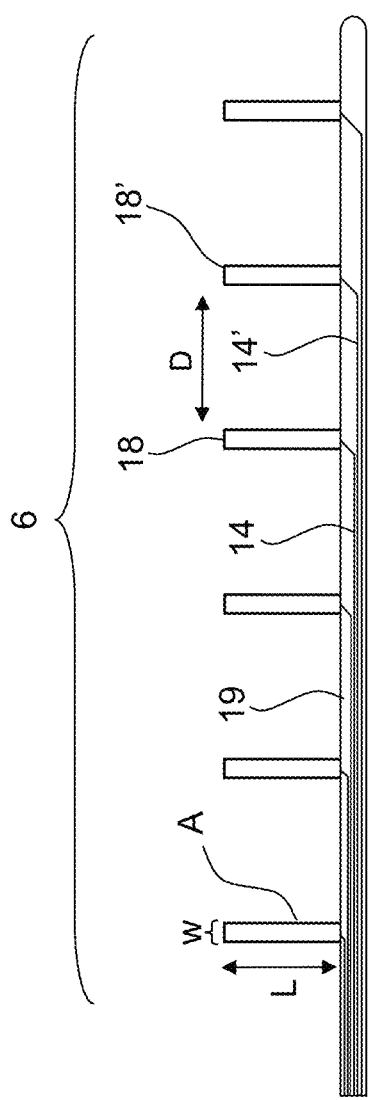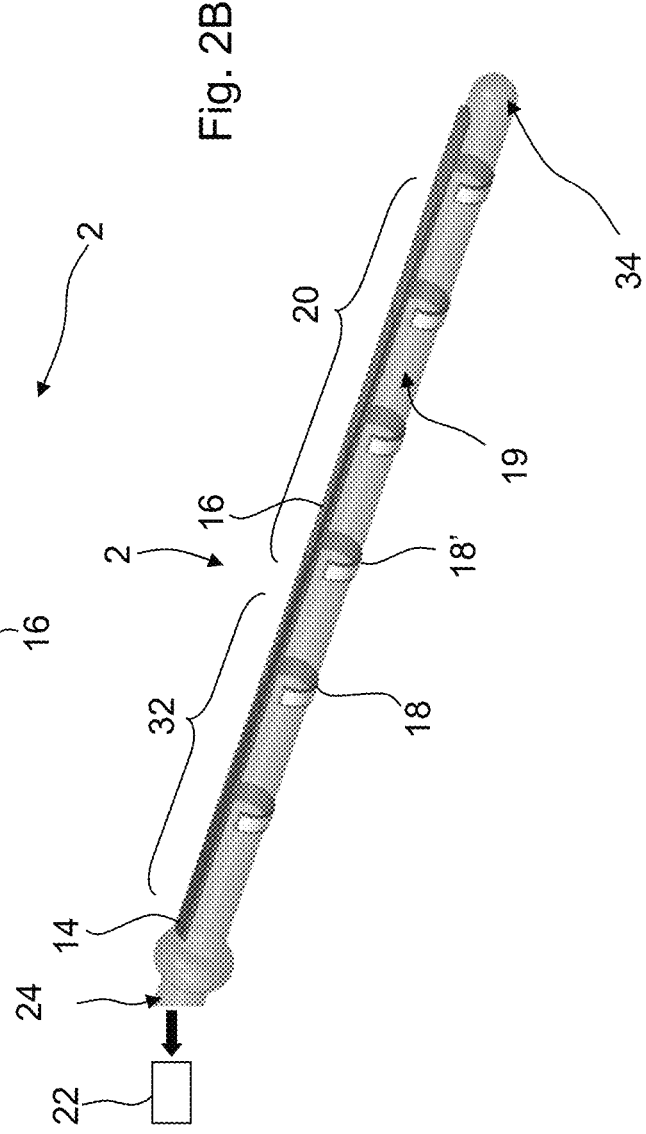

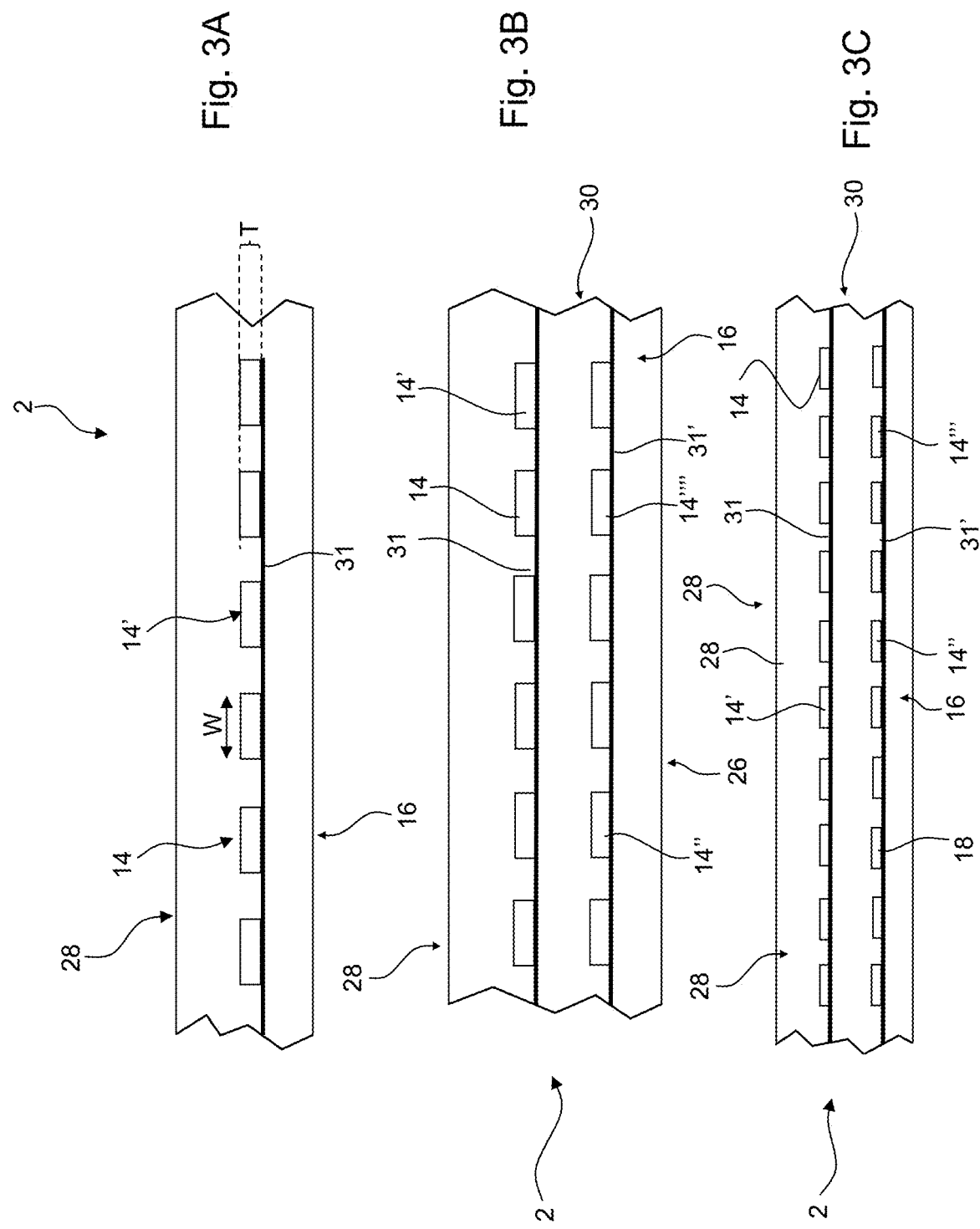

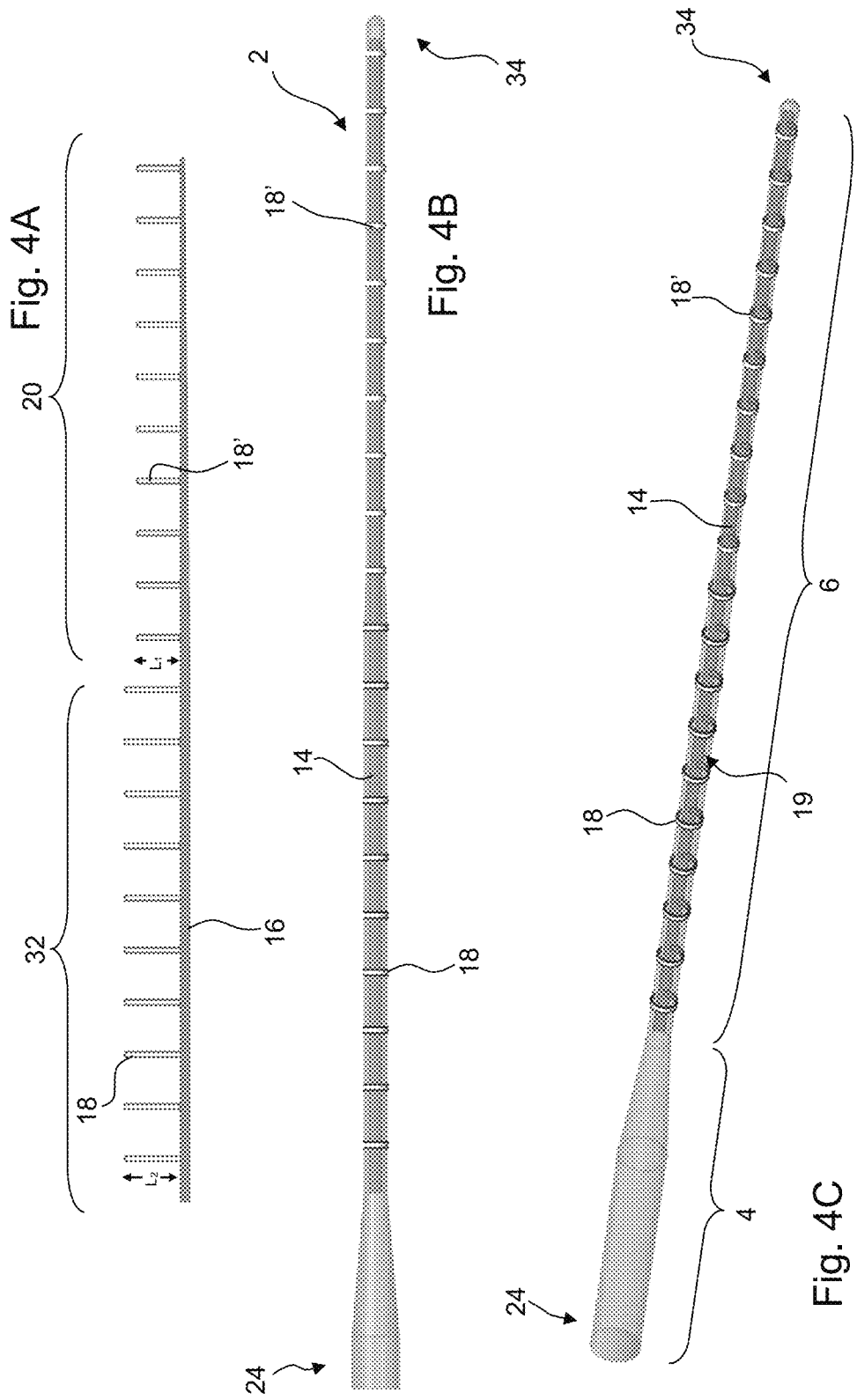

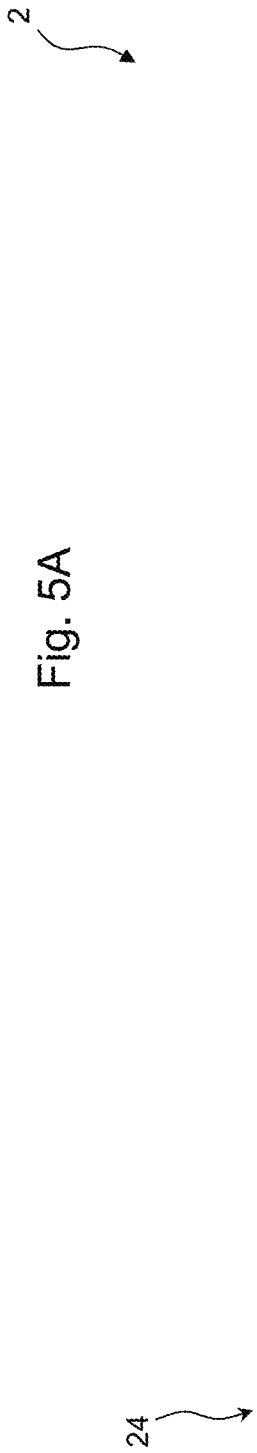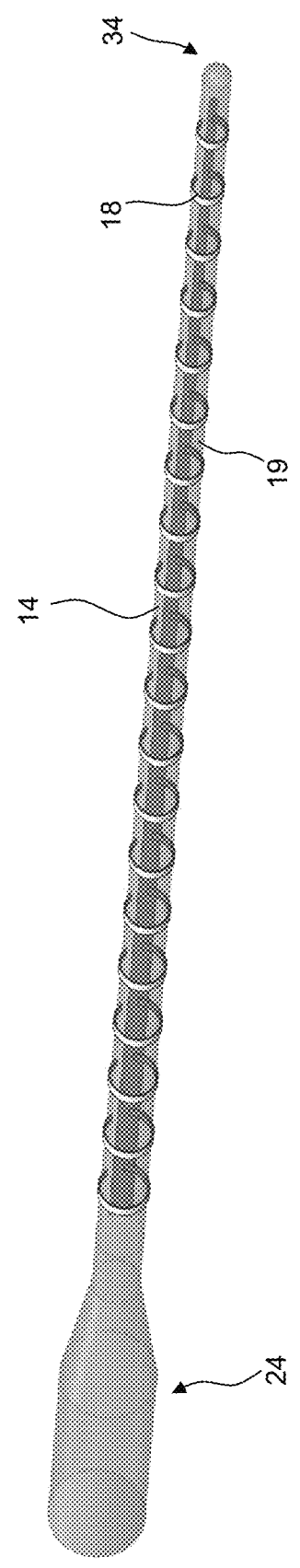

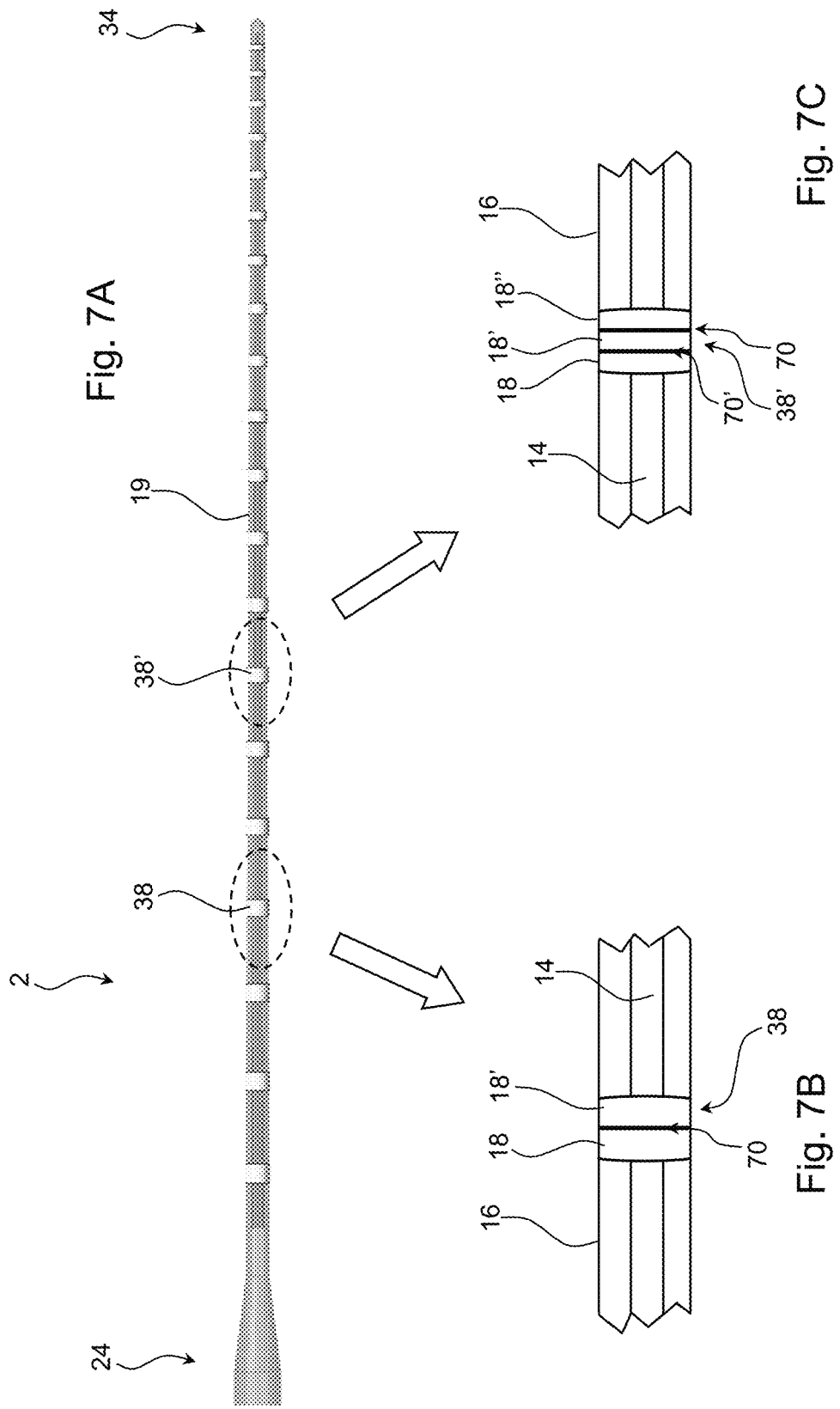

IMPLANTABLE ELECTRODE ARRAY

PRIORITY

This application claims priority to European Patent Application EP17201787.3, submitted on Nov. 15, 2017.

FIELD

The present disclosure relates to an implantable electrode array. More particularly, the disclosure relates to an implantable electrode array for a cochlear implant.

BACKGROUND

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how intense the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous auditory prosthesis systems (e.g., cochlear implant (CI) systems) have been developed. Auditory prosthesis systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, a lead having an array of electrodes disposed thereon may be implanted in the cochlea of a patient with the electrodes being distributed at various intra-cochlear positions. The electrode array is connected to an implantable stimulator unit that generates the electrical signals for delivery to the electrodes. The stimulator unit in turn is operationally connected to a signal processing unit which also contains a microphone for receiving audio signals from the environment, and for processing these signals to generate control signals for the stimulator. Typically, the signal processing unit is in practice, located externally to the patient and the stimulator is implanted within the patient, usually near the mastoid on the patient's skull and underneath the surrounding tissue. The processor and stimulator may communicate by various wireless means including by a radio frequency link.

The electrodes form a number of stimulation channels, each channel relating to an assigned frequency range, through which electrical stimulation pulses may be applied directly to auditory nerves within the cochlea. An audio signal may then be presented to the patient by translating the audio signal into a number of electrical stimulation pulses and applying the stimulation pulses directly to the auditory nerve within the cochlea via one or more of the electrodes.

As the electrode array is typically surgically implanted within the scala tympani of the cochlea of the recipient, the dimensions of the array and the manner of its insertion must be such so as to avoid damage to the sensitive structures of the cochlea. The dimensions and spiral shape of the cochlea also limit the maximum dimensions, particularly the diameter, and the stiffness of any array used as part of a cochlear implant.

In existing designs, this has limited the number of electrically conducting electrodes that can be incorporated into the array, due in the main to limitations imposed on the number of wires that can extend through the array to the electrodes. Traditional electrode array designs have required one or more conductive wires to be connected to each electrode and as such for an array having, for example 22 electrodes, the minimum number of wires required would be 22. With an increased understanding of the tonotopic nature and behavior of the cochlea, the benefits of providing an increased number of stimulating electrodes within the cochlea to stimulate more discrete sites within the cochlea are now being realized. For example, increasing the number of electrodes may provide granularity in assigned frequency range and/or to increase the total frequency range across different electrodes. Also, in a bilateral cochlear implant system, increasing the number of electrodes may allow for increasing the effect of sound localization and speech perception in spatially separated sounds.

However, it has been demonstrated that increasing the number of wires in conjunction with an increased number of electrodes unacceptably increases the dimensions and stiffness of the array. Merely reducing the diameter of the wires, in order to keep the overall dimensions unchanged, leads to an unacceptable decrease in lead resistance. As a result, this limitation on the number of leads, and hence electrodes, limits the scale and type of electrical stimulations that can be applied to the auditory nerve by the electrode array.

The present disclosure provides a solution to this problem by allowing an increase in the number of electrodes of an electrode array of a cochlear implant, while still providing an array to have a dimension that allows for insertion within a patient's cochlea.

SUMMARY

According to an aspect of the disclosure, the implantable electrode array comprises:
- a flexible electrically non-conductive carrier;
- a flexible electrically non-conductive substrate provided with a plurality of electrical tracks, wherein
  at least two of the plurality of electrical tracks run along different lengths of the flexible substrate and each of the plurality of electrical tracks is physically and electrically connected to a respective electrode contact of a plurality of electrode contacts, and
  the flexible substrate is immovably attached to and along a length of the flexible carrier.

The implantable electrode array comprises a flexible electrically non-conductive carrier. The carrier may preferably be made in silicone. The carrier may be made in another biocompatible flexible material.

It may be an advantage during insertion of the electrode array that at least a portion of the flexible electrically non-conductive carrier has a cylindrical geometry along a length of the electrode array.

The flexible electrically non-conductive substrate is provided with a plurality of electrical tracks. The electrical tracks may be made of gold. The flexible electrically non-conductive substrate may be made of a material allowing the substrate to have a small thickness and low mechanical stiffness. Such material may be selected from parylene-C, or polyimide, Polydimethylsiloxane (PDMS-silicone), Liquid Crystal Polymer (LCP), Polyetheretherketone (PEEK) or Polyesterimide (PEI).

At least two of the plurality of electrical tracks run along different lengths of the flexible substrate. Each of the plurality of electrical tracks is physically and electrically connected to a respective electrode contact of a plurality of electrode contacts. The electrode contacts may be made in different biocompatible materials such as platinum-iridium, gold, iridium oxide, graphene, or a biocompatible conducting plastic such as PEDOT-PSS. Each electrode contact may be wrapped around the flexible carrier and immovably attached on the flexible carrier in a wrapped state.

The flexible substrate is immovably attached to and along a length of the flexible carrier. This may be achieved using different known techniques such as gluing or direct overmolding.

The electrical tracks are attached to the carrier and the carrier around which the electrodes are wrapped does not include wires within itself. Therefore, the carrier in the electrode array according to the disclosure can be made thinner and more flexible than in the prior art electrode arrays that comprise wires.

According to another aspect of the disclosure, the plurality of electrode contacts are at least partially wrapped around the flexible carrier to define a plurality of electrodes that are spaced along the length of the flexible carrier.

Hereby, it is possible to arrange a plurality of electrode contacts as electrodes in a wrapped state around the flexible carrier. This allows for providing large electrode contacts having a large electrical contact area.

According to yet another aspect, the plurality of electrical tracks are spaced apart along a width of the flexible electrically non-conductive substrate. Hereby, it is possible to provide a number of electrodes having a larger number of channels compared with the prior art electrode arrays of same size.

According to a further aspect, the flexible electrically non-conductive substrate comprises a lengthwise at least substantially flat surface and the plurality of electrical tracks are arranged over the flat surface. Hereby, it is possible to start from a flat and simple flexible substrate, and to obtain a 3D structured electrode array with larger electrode areas compared with the prior art electrode arrays.

According to another aspect according to the disclosure, the plurality of electrical tracks are covered with an insulating material.

Hereby, it is possible to arrange the electrical tracks on the top of each other.

According to an even further aspect according to the disclosure, the flexibility of the electrode contacts allows the electrode contacts to be at least partially wrapped around the flexible carrier.

Hereby, it is possible to arrange the electrode contacts along the perimeter of the flexible carrier.

According to another aspect according to the disclosure, the length and/or flexibility of each of the plurality of electrode contacts is adapted in dependent on a perimeter of a section of the flexible carrier around which each of the plurality of electrode contacts is at least partially wrapped.

Hereby, it is possible to provide an electrode array, in which the electrode contacts extend along a predefined portion of the perimeter of the section of the flexible carrier around which each of the plurality of electrode contacts is at least partially wrapped.

By the term "adapted in dependent" is meant that the length of each of the plurality of electrode contacts is selected in such a manner that the electrode contacts can be at least partially wrapped around the perimeter of a section of the flexible carrier.

In one embodiment according to the disclosure, the electrode contacts extend along 50%, 55%, 60%, 65%, 70%, 75%, 80%, 85% 90% 95% or 100% of the perimeter of a section of the flexible carrier, around which the individual electrode contacts are wrapped.

According to a further aspect according to the disclosure, the flexible carrier is a solid body devoid of a hollow section or a hollow section without any component disposed therein at least along a length of the flexible substrate, where the flexible substrate is immovably attached to the flexible carrier.

Having an electrode array with a flexible carrier comprising a solid body devoid of a hollow section allows for obtaining a stronger electrode array. Having a hollow section without any component disposed therein allows for obtaining a very flexible electrode array.

In an embodiment, the flexible carrier may include a number of sections such that at least one section comprises a solid body devoid of a hollow section and at least other section comprises a hollow body without any component disposed therein at least along a length of the flexible substrate, where the flexible substrate is immovably attached to the flexible carrier. This allows for obtaining an electrode array that is adapted for both desired strength and flexibility. In a specific embodiment, the flexible carrier may include a number of sections such that at least one section is solid body devoid of a hollow section and at least other section is a hollow body without any component disposed therein at least along a length of the flexible substrate, where the flexible substrate is immovably attached to the flexible carrier and at least one section comprising the solid body is alternatively positioned to the at least one section comprising the hollow body, i.e. a solid body followed by a hollow body and then a solid body and so on.

According to an even further aspect according to the disclosure, the plurality of electrical tracks are arranged over a surface of the flexible substrate.

According to another aspect according to the disclosure, at least one electrode contact of the plurality of electrode contacts comprises at least one electrically non-conductive partition dividing the at least one electrode contact into at least two electrode parts.

Hereby, it is possible to provide a multipolar electrode.

According to a further aspect according to the disclosure, the implantable electrode array comprises a plurality of substrates, each comprising a plurality of electrical tracks, wherein each electrical track of the plurality of electrical tracks is physically and electrically connected to a respective electrode contact of a plurality of electrode contacts comprised by the respective flexible substrate of a plurality of substrates, each of the flexible substrate of the plurality of substrates is immovably attached to and along a length of the flexible carrier such that the plurality of substrates are spaced apart from each other, and the plurality of electrode contacts are at least partially wrapped around the flexible carrier to define a plurality of electrodes that are spaced from each other along the length of the flexible carrier.

According to another aspect according to the disclosure, the flexural modulus of elasticity of the flexible substrate is smaller than 5 GPa, preferably smaller than 3-4 GPa. Hereby, it is possibly to provide an electrode array being sufficiently flexible to be easily inserted into the cochlea.

According to a further aspect according to the disclosure, the width of the electrode contact is smaller than 0.3 mm, preferably smaller than 0.15-0.25 mm such as 0.2 mm. Hereby, it is possibly to provide an electrode array that is easily to insert into the cochlea.

According to another aspect according to the disclosure, the thickness of the electrode contact is smaller than 0.15 mm, preferably smaller than 0.04-0.06 mm such as 0.05 mm.

According to a further aspect according to the disclosure, the thickness of the carrier is smaller than 0.15 mm, preferably smaller than 0.04-0.06 mm such as 0.05 mm.

According to an embodiment, the thickness (T) of the electrode contact is same as the thickness of the electrical tracks.

The implantable medical device according to the disclosure is an implantable medical device comprising an implantable stimulator configured to be connected to an electrode array according to the disclosure.

According to one aspect according to the disclosure, the device is a cochlear implant system.

According to an embodiment, a method is disclosed. The method for manufacturing the electrode array includes
  providing a plurality of electrical tracks on a flexible electrically non-conductive substrate;
  providing at least two of the plurality of electrical tracks that run along different lengths of the flexible substrate such that each of the plurality of electrical tracks is physically and electrically connected to a respective electrode contact of a plurality of electrode contacts;
  immovably attaching the flexible substrate to and along a length of a flexible electrically non-conductive carrier;
  connecting, using the plurality of electrical tracks, the electrode contacts to a connection area that electrically connects to a stimulator unit; and
wrapping the plurality of electrical contacts around the flexible electrically non-conducting carrier to form electrodes.

According to one aspect according to the disclosure, the electrode array comprises
  a flexible electrically non-conducting carrier;
  a connection area that is configured to be electrically connected to a stimulator;
  an active area provided with a plurality of electrodes; and
  a plurality of electrical tracks electrically connecting the electrodes and the connection area, said electrodes being formed from flexible electrical contacts being wrapped around the flexible electrically non-conducting carrier.

According to a further aspect according to the disclosure, the cross-section of the flexible electrically non-conducting carrier is circular or oval.

According to an even further aspect according to the disclosure, the electrical contacts are C-shaped or O-shaped in the wrapped state and extend around the perimeter/cross sectional circumference of the flexible electrically non-conducting carrier.

According to another aspect according to the disclosure, the electrical tracks extend along the length of the flexible substrate.

According to a further aspect according to the disclosure, the flexible substrate is made in silicone.

According to another aspect according to the disclosure, the flexible substrate may be made of polyimide, the electrical tracks may be made of gold, and the electrical contacts may be made of a metallic material, preferably a metal such as gold or platinum.

According to another aspect according to the disclosure, the electrical contacts may be coated with organic material such as poly(3,4-ethylenedioxythiophene) (PEDOT) or Iridium Oxide, thus offering lower impedance, lower stimulation thresholds, higher sensitivity, higher charge density.

According to another aspect according to the disclosure, the electrode array comprises a plurality of parallel electrical tracks, wherein adjacent electrical tracks are spaced from each other along the width of the substrate.

According to an even further aspect according to the disclosure, the electrical tracks are substantially evenly spaced from each other.

According to an even further aspect according to the disclosure, the electrodes are evenly spaced from each other. According to an embodiment, the electrodes are unevenly spaced along length of the substrate. For example, the distance between consecutive electrodes progressively increases as the distance from tip of the electrode array increases.

According to another aspect according to the disclosure, the electrical tracks are attached to the outside surface of the flexible substrate, preferably by means of an adhesive, e.g. comprising silicone or another biocompatible flexible material.

According to an even further aspect according to the disclosure, the electrical contacts are attached to the outside surface of the flexible substrate, preferably by means of an adhesive, e.g. comprising silicone or another biocompatible flexible material.

According to another aspect according to the disclosure, the electrode array comprises an upper layer electrical track and a lower layer electrical track, wherein the upper layer electrical track and the lower layer electrical track preferably extend parallel to each other, wherein a first portion of the electrical contacts are electrically connected to said an upper layer electrical track and wherein the remaining portion of the electrical contacts are electrically connected to said lower layer electrical track.

According to an even further aspect according to the disclosure, a first portion of the electrical contacts have a first dimension (length or diameter), wherein the remaining portion of the electrical contacts have another smaller dimension (length or diameter).

According to another aspect according to the disclosure, the dimension (length or diameter) of the electrical contacts gradually decreases towards the distal portion, i.e. closer to the tip, of the electrode array. The flexible substrate may have a conical shape being tapered towards the distal portion of the electrode array.

According to an even further aspect according to the disclosure, the width of the electrical contacts gradually decreases towards the distal portion, i.e. closer to the tip, of the electrode array. The flexible substrate may have a conical shape being tapered towards the distal portion of the electrode array.

According to another aspect according to the disclosure, the distance between adjacent electrical contacts gradually decreases towards the distal portion, i.e. closer to the tip, of the electrode array. The flexible substrate may have a conical shape being tapered towards the distal portion of the electrode array.

According to an even further aspect according to the disclosure, the electrode array includes a plurality of multipolar electrodes each comprising several electrodes.

According to another aspect according to the disclosure, wherein the electrode array comprises a plurality of electrodes defined by a plurality of the electrical contacts wrapper around the carrier. The number of electrodes may vary between 10-30 electrodes, preferably 12-28 electrodes, such as 14-26 electrodes. It is apparent that the number of electrodes may vary.

According to one aspect according to the disclosure, a cochlear implant system is disclosed. The cochlear implant system includes a sound processor comprising a microphone or a microphone array. The microphone or microphone array is configured to receive a sound and to generate a microphone signal in response to the received sound. The sound processor is further configured to process the microphone signal and produce a processed signal.

In one embodiment comprising an external sound processor, the sound processor is configured to be positioned at or in the vicinity of an ear of the user of the cochlear implant system and communicatively coupled via an electromagnetic coupling to an implantable stimulator that is configured to generate stimulation pulses in accordance with the processed microphone signal. The cochlear implant system may further include the electrode array disclosed previously and claimed in the application. The electrode array is configured to be inserted into the scala tympani of the user and to deliver stimulation pulses using the electrodes defined by electrode contacts wrapped around the carrier.

In another embodiment comprising an implantable sound processor, the sound processor is configured to also act as a stimulator and to generate stimulation pulses. The cochlear implant system may further include the electrode array disclosed previously and claimed in the application. The electrode array is configured to be inserted into the scala tympani of the user and to deliver the stimulation pulses using the electrodes defined by electrode contacts wrapped around the carrier.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

FIG. 1A shows a side view of a prior art cochlear implant electrode array;

FIG. 1B shows a close-up view of the central portion of the prior art cochlear implant electrode array shown in FIG. 1A;

FIG. 1C shows a schematic view of a cochlear implant system and an external sound processor connected thereto;

FIG. 2A shows a schematic view of an implantable electrode array;

FIG. 2B shows a perspective, side view of an implantable electrode array;

FIG. 3A shows a cross section of an implantable electrode array showing the electrical tracks;

FIG. 3B shows a cross section of a multi-layer implantable electrode array showing the electrical tracks;

FIG. 3C shows a cross section of a multi-layer implantable electrode array showing the electrical tracks;

FIG. 4A shows a side view of a portion of an implantable electrode array in a first configuration;

FIG. 4B shows a side view of the implantable electrode array shown in FIG. 4A, in another configuration;

FIG. 4C shows a perspective view of the implantable electrode array shown in FIG. 4B;

FIG. 5A shows a side view of an implantable electrode array;

FIG. 5B shows a perspective view of the implantable electrode array shown in FIG. 5A;

FIG. 7A shows a side view of an implantable electrode array with unevenly distributed electrodes having different physical dimensions;

FIG. 7B shows a close-up view of a multipolar electrode of the implantable electrode array shown in FIG. 8A; and FIG. 7C shows a close-up view of another multipolar electrode of the implantable electrode array shown in FIG. 8A.

DETAILED DESCRIPTION

Figure 6A:
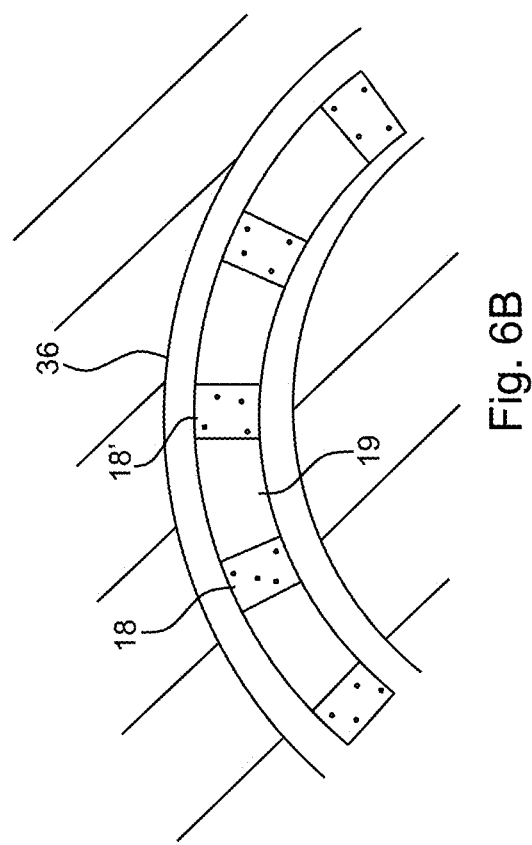
FIG. 6A shows a cross-sectional view of an implantable electrode array in a bent configuration.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, modules, components, steps, processes, etc. (collectively referred to as "elements"). Depending upon particular application, design constraints or other reasons, these elements may be implemented using element different from the one disclosed in the application.

FIG. 1A illustrates a side view of a prior art cochlear implant electrode array 102 comprising a connection area 104 and an active zone 106. FIG. 1B illustrates a close-up view of the central portion of the prior art cochlear implant electrode 102 array shown in FIG. 1A, whereas FIG. 1C illustrates a schematic view of a cochlear implant system 44 and an external sound processor 50 connected thereto.

A lead 110 extends through the connection area 104 and is electrically connected to the active zone 106 by means of a plurality of connection wires (not shown) contained within the cylindrical geometry defining the active zone, the connection wires connecting each electrode such as 108/108' to the connection area. The lead 110 is configured to be electrically connected to a cochlear stimulator 22 by means of a lead 48, thus providing an electrical connection between the electrodes and stimulator.

As shown in FIG. 1C, the connection area 104 has to be arranged between the middle ear and the cochlea 42. Therefore, the connection area 104 has to be resistant to the handling with a micro forceps during surgery and to the bone growth consequently to the surgery. Two silicone rings 112, 112' are provided in the connection area 104 in order to facilitate the insertion of the electrode array 102 into the cochlea 42. A surgeon can push the silicone rings 112, 112' with a sharp and fine teeth of a tool (fork) during insertion of the electrode array into the cochlea. When the electrode array 102 has been fully inserted into the cochlea 42, the silicone rings 112, 112' close the cochleostomy to avoid the loss of perilymph and that a pathogen agent comes into the cochlea 42 and causes infection.

The active area 106 is configured to be inserted into the cochlea duct of the cochlea 42. The active area 106 comprises a plurality of electrodes for example twenty active electrodes 108, 108' made of platinum-iridium which is a biocompatible material, stable and approved for being used in active implantable medical devices. The electrode array 102 needs to be small enough to be inserted as far as possible into the cochlea 42.

The cochlear implant system 44 shown in FIG. 1C comprises an electrode array 102 connected to a cochlear stimulator 22 by means of a lead 48. In the illustration, the electrode array 102 has already been inserted into the cochlea 42. A behind-the-ear sound processor 50 is configured to be arranged behind the outer ear 40 is connected to an electromagnetic coupling 52 arranged at the skin in a close distance from the cochlear stimulator 22.

Now referring to FIG. 2B, which illustrates a schematic view of an implantable electrode array 2 according to an embodiment. The electrode array 2 comprises a flexible electrically non-conductive carrier 19. The flexible electrically non-conductive carrier 19 comprises a flexible electrically non-conductive substrate 16 attached thereto. A plurality of electrical tracks 14, 14' extend to a different distance along a length of the flexible substrate 16 (as shown in FIG. 2A). Each of the plurality of electrical tracks 14, 14' has different length and is physically and electrically connected to a corresponding electrode contact 18, 18'. The flexible substrate 16 is immovably attached to the flexible carrier 19 and extend along a least to a certain length or entire length of the flexible carrier 19.

The electrode array 2 comprises an active area 6 defined by the length of the substrate and a distal end 34. The electrical tracks 14, 14' are configured to be connected to a cochlear stimulator 22 in the end 24, opposite to the distal end 34, of the electrode array 2.

The electrode array 2 comprises a plurality of electrical contacts 18, 18' that may be evenly or unevenly distributed along a length of the substrate (see FIGS. 4B and 5A showing evenly distributed electrodes and FIG. 7A showing unevenly distributed electrodes). For illustrative purposes six evenly distributed electrode contacts 18, 18' are shown. Accordingly, the distance D between adjacent electrode contacts 18, 18' is variable or constant.

The width W of the electrode contacts 18, 18' determines the dimension of the electrode contacts 18, 18' along the scala tympani. The length L of the electrode contacts 18, 18' is designed in accordance with the circumference of the electrode when it is rolled and shaped as shown in FIG. 2b.

The area A of the electrode contacts 18, 18' is given by the product of the length L and the width W. The electrode contacts 18, 18' can be made of different biocompatible materials, such as platinum-iridium, gold, iridium oxide, graphene, or a biocompatible material made of a biocompatible conducting plastic such as PEDOT-PSS.

In order to adapt the electrode array 2 to the scala tympani length of a human cochlea, the electrode array 2 may include at least 20 electrodes with a 1.2 mm pitch between the electrodes, in order to cover a length of 24 mm of scala tympani. In another embodiment according to the disclosure, the electrode array 2 may have 24 electrodes with a different pitch (e.g. lower than 1.2 mm) in order to cover a specific range of cochlea length.

The flexible substrate 16 is immovably arranged on the flexible carrier 19. The electrode array 2 comprises electrical tracks 14 attached on the flexible carrier 19. In one embodiment, the electrical tracks 14 are attached to the flexible carrier 19 by an attaching means such as glue. The flexible carrier 19 may be made of silicone or another biocompatible flexible material. Each electrical track 14 of the electrode array 2 is electrically connected to a respective electrode contact 18, 18'. Each electrode contact 18, 18' is wrapped around the flexible carrier 19 and attached thereto, e.g. by an attaching means such as glue.

Accordingly, the electrode array 2 comprises electrode contact 18, 18' extending around the circumference of a specific section of the flexible carrier 19, thus defining a plurality of electrodes 18, 18', as illustrated in FIG. 2B. The electrode array 2 is provided with larger electrode areas A in this rounded shape, i.e. in wrapped state around the carrier 19 when compared to a flat shaped electrode provided only on a surface of the substrate.

FIG. 3A illustrates a cross section of an implantable electrode array 2 showing the electrical tracks. The electrode array 2 comprises a top layer 28 covering a plurality of electrical tracks 14, 14' and may thus act as the insulating material covering the electrical tracks. The electrical tracks 14, 14' are connected to a wire 31 connecting the plurality of electrical tracks to a stimulator. The top layer 28 is bonded on a bottom layer 16, which may act as the flexible substrate. The electrode array 2 comprises a number of electrode contacts such as six electrode contacts individually connected to respective electrical tracks 14, 14', which may have a width W and a thickness T.

The electrode array 2 may comprises 12, 16, 18, 20, 24 or more electrical tracks 14, 14', which are individually connected to electrode contacts.

FIG. 3B shows a cross section of a multi-layer implantable electrode array showing the electrical tracks, and FIG. 3C shows a cross section of a multi-layer implantable electrode array showing the electrical tracks.

Both FIG. 3B and FIG. 3C illustrates a portion of a multi-layer electrode array, in which the electrode array 2 comprises electrical tracks 14, 14', 14", 14''' and corresponding wires 31, 31', arranged in at least two preferably parallel layers, connecting respective electrical tracks to the stimulator. The electrical tracks 31, 31' are individually connected to respective electrode contacts in two spatially separated preferably parallel layers.

The multi-layer electrode array 2 comprises a bottom layer 16 made of flexible and insulating material acting as a substrate on which a first plurality of electrical tracks 14", 14''' are provided. Each of the electrical tracks 14", 14''' are individually connected to a first plurality of electrode contacts (not shown). An intermediate layer 30 made of flexible and insulating material, acting as the insulating material, covers the first plurality of electrical tracks 14", 14'''. A second plurality of electrical tracks 14, 14' are arranged over the intermediate layer 30, which acts as a substrate for the second plurality of electrical tracks 14, 14'. The second plurality of electrical tracks 14, 14' are individually connected to a second plurality of electrode contacts (not shown). The second plurality of electrical tracks 14, 14' are covered with a top layer 28, which as acts as the insulating material for the second plurality of electrical tracks. The intermediate layer 30 is bonded such as by glue to the bottom layer 16 and the top layer 28 is bonded to the intermediate layer 30. The wire 31' is arranged to electrically connect the first plurality of electrical tracks 14", 14''' to the stimulator and the wire 31" is arranged to electrically connect the second plurality of electrical tracks 14, 14' to the stimulator. Each of the electrode contacts from the plurality of first electrode contacts and the plurality of second electrode contacts are wrapped around the flexible carrier (not shown) to form first plurality of electrodes and second plurality of electrodes respectively.

In one embodiment, the multi-layer electrode array 2 comprises a plurality of electrical tracks such as six electrical tracks 14, 14', 14", 14''' and six electrode contacts for each layer, thereby allowing for obtaining a multi-layer electrode array comprising 12 electrodes, as shown in FIG. 3B. In one embodiment, the multi-layer electrode array 2 comprises a plurality of electrical tracks such as ten electrical tracks 14, 14', 14", 14''' and ten electrode contacts for each layer, thereby allowing for obtaining a multi-layer electrode array comprising 20 electrodes, as shown in FIG. 3C. In another embodiment, the three-layer electrode array 2 comprises eight electrical tracks and electrode contacts for each layer. Accordingly, the multi-layer electrode array 2 will comprise twenty-four electrodes.

FIG. 4A illustrates a side view of a portion of an implantable electrode array 2 according to the disclosure in a first configuration. FIG. 4B illustrates a side view of the implantable electrode array 2 shown in FIG. 4A, in another configuration, whereas FIG. 4C illustrates a perspective view of the implantable electrode array 2 shown in FIG. 4B.

The electrode array 2 comprises a flexible electrically non-conductive substrate 16 a plurality of electrical tracks 14 extending the length of the flexible substrate 16. Each of the plurality of electrical tracks 14 is physically and electrically connected to a respective electrode contact 18, 18'.

In FIG. 4A, it can be seen that the electrode array 2 comprises an active area 6 that includes a proximal portion 32 provided next to a distal portion 20 provided close to the distal end 34 of the electrode array 2. Generally, the diameter of the distal portion of the active area 6 of the electrode array 2 is smaller than the diameter of the proximal portion of the active area 6 of the electrode array 2, therefore the length $L_2$ of the electrode contacts 18 in the proximal portion 32 is preferably larger than the length $L_1$ of the electrode contacts 18' in the distal portion 20. Accordingly, in FIG. 4B and FIG. 4C, the varied length of electrode contacts 18, 18' allow for arranging an electrode such that the corresponding electrode contact sufficiently wraps around the circular path at the periphery of the flexible carrier 19, thus provide adequate electrode surface area. The electrode contacts 18, 18' are evenly distributed along the length of the active portion of the electrode array 2. Accordingly, the adjacent electrode contacts 18, 18' are equally spaced from each other. In another embodiment, the electrode may be distributed unevenly along the length of the carrier.

FIG. 5A illustrates a side view of an implantable electrode array 2 according to the disclosure, wherein FIG. 5B illustrates a perspective view of the implantable electrode array 2 shown in FIG. 5A. The electrode array 2 comprises a flexible electrically non-conductive carrier 19 and a plurality of electrical tracks 14 extending the length of the flexible substrate on which the electrical tracks are arranged. Each of the plurality of electrical tracks 14 is physically and electrically connected to a respective electrode contact 18.

Generally, the diameter of the carrier gradually decreases from the proximal end 24 to the distal end 34 along the length of the carrier 19, therefore, the length of the electrode contacts is adapted to decrease gradually from the proximal end 24 to the distal end 34. The electrode contacts 18 are shown to be evenly distributed along the length of the active portion of the electrode array 2. Accordingly, the adjacent electrode contacts 18 are equally spaced from each other. In another embodiment, the electrode may be distributed unevenly along the length of the carrier. As shown in FIG. 5B, the gradually changing length of electrode contacts 18, 18' along length of the carrier allows for arranging an electrode such that the corresponding electrode contact sufficiently wraps around the circular path at the periphery of the flexible carrier 19, thus provide adequate electrode surface area.

Figure 6B:
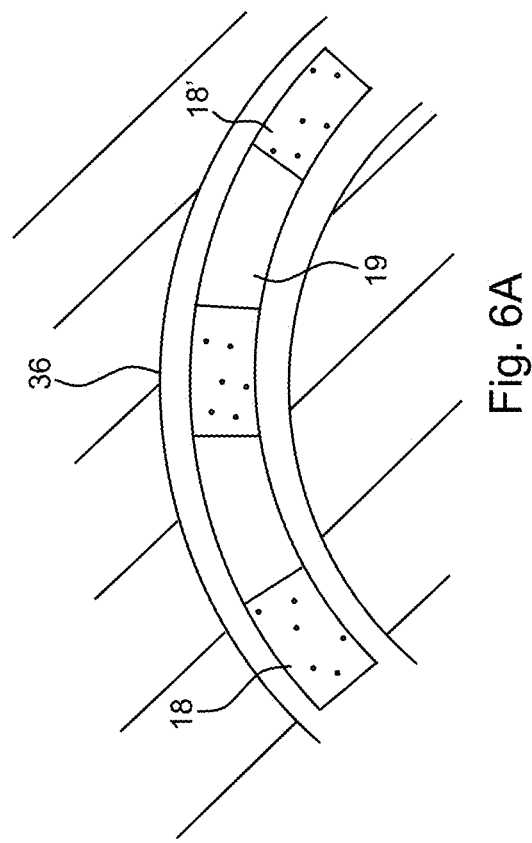
FIG. 6B shows a cross-sectional view of another implantable electrode array in a bent configuration.

FIG. 6A illustrates a cross-sectional view of a portion of an implantable electrode array 2 in a bent configuration and FIG. 6B illustrates a cross-sectional view of another implantable electrode array 2 according to the disclosure in a bent configuration. Both in FIG. 6A and in FIG. 6B, the electrode array 2 is arranged into the same curvature of the cochlea 36.

In FIG. 6A, the electrode array 2 comprises larger electrode contacts 18, 18' than the electrode array 2 shown in FIG. 6B.

FIG. 7A illustrates a side view of an implantable electrode array 2, whereas FIG. 7B illustrates a close-up view of a multipolar electrode 38 of the implantable electrode array 2 shown in FIG. 7A and FIG. 7C illustrates a close-up view of another multipolar electrode 38 of the implantable electrode array 2 shown in FIG. 8A. FIG. 7A further illustrates electrodes that are unevenly distributed along the length of the substrate. The electrodes may also have different physical dimensions comprising at least one of diameter or width, as shown in FIG. 7A. It is apparent that such variation in physical dimensions and distribution is not limited to multipolar electrodes and may also be employed for electrodes that are disclosed earlier in the description with respect to non-multi-polar electrodes. In another embodiment, the multi-polar electrodes are evenly distributed along the length of the substrate.

The electrode array 2 comprises a flexible electrically non-conductive carrier 19 around with a plurality of electrical contacts are wrapped to form a plurality of electrodes. Each of the plurality of electrical tracks 14 is physically and electrically connected to a respective electrode contact 18, 18', 18".

The length of the electrode contacts 18, 18', 18" in each multipolar electrode 38, 38' gradually decreased from the first end 24 of the electrode array 2 towards the distal end 34 of the electrode array 2. The distance between adjacent multipolar electrodes 38, 38' may gradually decreases towards the distal end of the active portion of the electrode array 2.

As shown in FIG. 7B the multipolar electrode 38 such as a bipolar electrode 38 comprises a first electrode contact 18 and a second electrode contact 18'. As shown in FIG. 7C the multipolar electrode 38' such as a tripolar electrode comprises a first electrode contact 18, a second electrode contact 18' and a third electrode contact 18". In an embodiment, the multipolar electrode includes at least two electrodes abutting one another with an insulation component 70, 70' therebetween. The insulation component may be a component that is different from any part of the carrier 19. The insulation component may arranged to divide an electrode into at least two electrodes.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, elements, components, and/or steps but do not preclude the presence or addition of one or more other features, elements, components, and/or steps thereof. It will also be understood that when an element is referred to as being "connected" or "coupled" to another element, it can be directly connected or coupled to the other element but an intervening elements may also be present, unless expressly stated otherwise. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The scope should be judged in terms of the claims that follow.

The invention claimed is:

1. An implantable electrode array comprising:
   a flexible electrically non-conductive carrier;
   a flexible electrically non-conductive substrate provided with a plurality of electrical tracks, wherein
   at least two of the plurality of electrical tracks run along different lengths of the flexible substrate and each of the plurality of electrical tracks is physically and electrically connected to a respective electrode contact of a plurality of electrode contacts,
   the flexible substrate is immovably attached to and along a length of the flexible carrier,
   the plurality of electrode contacts are at least partially wrapped around the flexible carrier to define a plurality of electrodes that are spaced along the length of the flexible carrier,
   a diameter of a proximal portion of an active area of the electrode array, where one of the at least two of the plurality of electrical tracks terminates, is larger than a diameter of a distal portion of the active area of the electrode array, where another of the at least two of the plurality of electrical tracks terminates, and
   the electrode contact, which is electrically connected to the one of the at least two of the plurality of electrical tracks, has a longer length in a circumferential direction than the electrode contact, which is electrically connected to the other of the at least two of the plurality of electrical tracks, to accommodate for the different diameters of the proximal portion and the distal portion of the active area of the electrode array.

2. The implantable electrode array according to claim 1, wherein the plurality of electrical tracks are spaced apart along a width of the flexible electrically non-conductive substrate.

3. The implantable electrode array according to claim 1, wherein the flexible electrically non-conductive substrate comprises a lengthwise at least substantially flat surface and the plurality of electrical tracks are arranged over the at least substantially flat surface.

4. The implantable electrode array according to claim 1, wherein the plurality of electrical tracks are covered with an insulating material.

5. The implantable electrode array according to claim 1, wherein the electrode contacts are flexible to allow the electrode contacts to be at least partially wrapped around the flexible carrier.

6. The implantable electrode array according to claim 1, wherein length and/or flexibility of each of the plurality of electrode contacts is adapted in dependent on a perimeter of a section of the flexible carrier around which each of the plurality of electrode contacts is at least partially wrapped.

7. The implantable electrode array according to claim 1, wherein the flexible carrier is a solid body devoid of a hollow section or a hollow section without any component disposed therein at least along a length of the flexible substrate, where the flexible substrate is immovably attached to the flexible carrier.

8. The implantable electrode array according to claim 1, wherein the plurality of electrical tracks are arranged over a surface of the flexible substrate.

9. The implantable electrode array according to claim 1, wherein at least one electrode contact of the plurality of electrode contacts comprises at least one electrically non-conductive partition dividing the at least one electrode contact into at least two electrode parts.

10. The implantable electrode array according to claim 1, further comprising a plurality of substrates, each comprising a plurality of electrical tracks, wherein each electrical track of the plurality of electrical tracks is physically and electrically connected to a respective electrode contact of a plurality of electrode contacts comprised by the respective flexible substrate of a plurality of substrates, each of the flexible substrate of the plurality of substrates is immovably attached to and along a length of the flexible carrier such that the plurality of substrates are spaced apart from each other, and the plurality of electrode contacts are at least partially wrapped around the flexible carrier to define a plurality of electrodes that are spaced from each other along the length of the flexible carrier.

11. The electrode array according to claim 1, wherein
   the flexural modulus of elasticity of the flexible substrate is smaller than 5 GPa, and/or
   the width of the electrode contact is smaller than 0.3 mm, and/or
   the thickness of the electrode contact is smaller than and/or the thickness of the carrier is smaller than 0.15 mm, and/or
   the thickness of the electrode contact is same as the thickness of the electrical tracks.

12. An implantable medical device comprising an implantable stimulator configured to be connected to an electrode array according to claim 1.

13. The implantable medical device according to claim 12, wherein the device is a cochlear implant system.

14. A method for manufacturing an electrode array comprising
   providing a plurality of electrical tracks on a flexible electrically non-conductive substrate;
   providing at least two of the plurality of electrical tracks that run along different lengths of the flexible substrate such that each of the plurality of electrical tracks is physically and electrically connected to a respective electrode contact of a plurality of electrode contacts, immovably attaching the flexible substrate to and along a length of a flexible electrically non-conductive carrier;

connecting, using the plurality of electrical tracks, the electrode contacts to a connection area that electrically connects to a stimulator unit; and wrapping the plurality of electrical contacts around the flexible electrically non-conducting carrier to form electrodes, wherein a diameter of a proximal portion of an active area of the electrode array, where one of the at least two of the plurality of electrical tracks terminates, is larger than a diameter of a distal portion of the active area of the electrode array, where another of the at least two of the plurality of electrical tracks terminates, and the electrode contact, which is electrically connected to the one of the at least two of the plurality of electrical tracks, has a longer length in a circumferential direction than the electrode contact, which is electrically connected to the other of the at least two of the plurality of electrical tracks, to accommodate for the different diameters of the proximal portion and the distal portion of the active area of the electrode array.

15. The method according to claim 14, wherein the plurality of electrical tracks are provided so as to be spaced apart along a width of the flexible electrically non-conductive substrate.

16. The method according to claim 14, wherein the flexible electrically non-conductive substrate comprises a lengthwise at least substantially flat surface and the plurality of electrical tracks are arranged over the at least substantially flat surface.

17. The implantable electrode array according to claim 2, wherein the flexible electrically non-conductive substrate comprises a lengthwise at least substantially flat surface and the plurality of electrical tracks are arranged over the at least substantially flat surface.

18. The method according to claim 14, wherein the plurality of electrical tracks are covered with an insulating material.

19. The implantable electrode array according to claim 2, wherein the plurality of electrical tracks are covered with an insulating material.

* * * * *